(12) United States Patent
Dobbs et al.

(10) Patent No.: US 6,455,460 B1
(45) Date of Patent: *Sep. 24, 2002

(54) RUTHENIUM CATALYSTS AND METHOD FOR MAKING SAME

(75) Inventors: Daniel A. Dobbs, Metuchen; Koenraad P. M. Vanhessche, Basking Ridge, both of NJ (US); Valentin Rautenstrauch, Bernex (CH)

(73) Assignee: Firmenich SA, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/690,980

(22) Filed: Oct. 18, 2000

Related U.S. Application Data

(63) Continuation of application No. 09/081,013, filed on May 19, 1998, now Pat. No. 6,214,763.
(60) Provisional application No. 60/047,168, filed on May 20, 1997.

(51) Int. Cl.⁷ ................................................. B01J 31/00
(52) U.S. Cl. ....................................... 502/155; 502/162
(58) Field of Search .................................. 502/155, 162

(56) References Cited

U.S. PATENT DOCUMENTS

| | | | |
|---|---|---|---|
| 5,304,524 A | 4/1994 | Klobucar et al. | 502/167 |
| 5,324,850 A | 6/1994 | Juge et al. | 556/21 |
| 5,563,308 A | 10/1996 | Spindler et al. | 585/277 |
| 5,563,309 A | 10/1996 | Togni et al. | 585/277 |
| 5,614,641 A | 3/1997 | Genet et al. | 549/313 |
| 5,728,866 A | 3/1998 | Rautenstrauch et al. | 560/122 |
| 6,043,380 A | 3/2000 | Okeda et al. | 502/162 |
| 6,214,763 B1 * | 4/2001 | Dobbs et al. | 502/155 |

FOREIGN PATENT DOCUMENTS

| | | |
|---|---|---|
| FR | 2 693 190 | 1/1994 |
| JP | 55-61937 | 5/1980 |
| WO | WO 91/02588 | 3/1991 |
| WO | WO 96/00206 | 1/1996 |
| WO | WO 97/18894 | 5/1997 |

OTHER PUBLICATIONS

B. Heiser et al., "New Efficient Methods for the Synthesis and In–Situ Preparation of Ruthenium (II) Complexes of Atropisometric Diphosphines and Their Application Catalytic Hydrogenations", *Tetrahedron: Asymmetry* vol. 2, No. 1, 51–62 (1991).

* cited by examiner

*Primary Examiner*—Mark L. Bell
*Assistant Examiner*—J. Pasterczyk
(74) *Attorney, Agent, or Firm*—Winston & Strawn

(57) ABSTRACT

A catalyst of ruthenium (II) comprising bidentate phosphine ligands is described which is obtained by a process that comprises treating equimolar amounts of an appropriate Ru complex and a bidentate diphosphine ligand with an acid of the formula H-Anion, wherein the anion is a non-coordinating anion, said acid being used in a ratio of 1 molar equivalent per mole of Ru complex and the treatment being carried out in a non-coordinating or weakly coordinating medium, under an oxygen-free atmosphere. Said catalyst is useful for the preparation of the preferred isomer of the Hedione®, having the configuration (+)-(1R)-cis, and of many other substrates comprising highly hindered carbon-carbon double bonds.

17 Claims, No Drawings

RUTHENIUM CATALYSTS AND METHOD FOR MAKING SAME

CROSS-REFERENCE TO RELATED APPLICATIONS

This application is a continuation of application Ser. No. 09/081,013 filed May 19, 1998, now U.S. Pat. No. 6,214,763 which claims the benefit of provisional application 60/047, 168 filed May 20, 1997.

FIELD OF THE INVENTION AND PRIOR ART

The present invention relates to the field of asymmetric hydrogenation and, more particularly, to the use of novel Ru(II) chiral catalysts for the asymmetric hydrogenation of substrates which, as a result of their weak donor capability and of their hindered structures, have proved heretofore very difficult or impossible to hydrogenate.

A great number of chiral metal catalysts has been used in the past to asymmetrically hydrogenate a variety of substrates.

In the context of the present invention, we can cite in particular the efforts of two research groups which actively studied the synthesis of Ru(II) chiral catalysts, obtained from the Ru(II) complex of formula [(COD)Ru(2-methylallyl)$_2$] (COD=cyclo-1,5-octadiene).

Thus, J.-P. Genet and his collaborators have published work related to catalysts of formula [Ru(P*-P*)(2-methylallyl)$_2$], wherein P*-P* represents a diphosphine ligand of the type of those currently known under abbreviated designations such as DIOP, CHIRAPHOS, PROPHOS, BDPP, CBD, NORPHOS, DEGUPHOS, BPPM, BINAP, R-DuPHOS (R=methyl or ethyl), BIPHEMP or yet DIPAMP (see, for example, J.-P. Genet et al., Tetrahedron : Asymmetry 1991, 2, 43). Such catalysts were obtained by heating the above-mentioned Ru(II) complex together with the appropriate chelating diphosphine, in a solvent such as hexane or toluene, such as to replace the cyclooctadiene with the chiral phosphine.

Upon subsequent work (see, for example, WO 91/02588; J.-P. Genet, Acros Organics Acta, 1994, 1, 1–8; J.-P. Genet et al., Tetrahedron: Asymmetry, 1994, 5, 665–690), these authors described the transformation of such catalysts via protonation by means of aqueous acids such as HBr, HCl, HF or HBF$_4$, in strongly coordinating solvents, capable of playing a role in stabilizing the coordination structure around the metal, which structure, according to the same authors, is of the hexacoordinate type. This kind of catalysts, which can be prepared in situ, proved to be useful for the asymmetric hydrogenation, in protic or strongly electron-donating solvents (methanol, ethanol or their mixtures with other solvents), of substrates comprising carbonyl groups and acyclic ethylenic bonds.

Other studies (see, for example, F. Heiser et al., Tetrahedron: Asymmetry, 1991 2, 51–62; EP 643 052; EP 398 132; EP 570 674) have resulted in reports of the use of catalysts prepared in situ for hydrogenating a variety of substrates, starting from the same ruthenium complex, but following a process according to which a mixture of said complex and an appropriate diphosphine ligand is treated with namely CF$_3$COOH, once again in an electron-donor solvent able to stabilize the coordinating structure of the metal.

These catalysts, and others obtained according to similar processes described in the cited references, reveal themselves very efficient in the asymmetric hydrogenation of various substrates, often good electron-donor substrates capable of coordinating the Ru(II), and are typically used with protic solvents, or mixtures of protic and aprotic solvents. However, they proved to be inefficient when used, under the prior art conditions, for the hydrogenation of substrates possessing heavily hindered ethylenic bonds, for example tetrasubstituted double bonds, in particular when the latter are part of ring systems.

In published International patent application No. WO 97/18894, filed on Nov. 20, 1996, we describe new Ru(II) catalysts and teach their successful use for asymmetrically hydrogenating this type of particularly hindered substrates. More particularly, there is described the hydrogenation of cyclopentenone derivatives of formula(II).

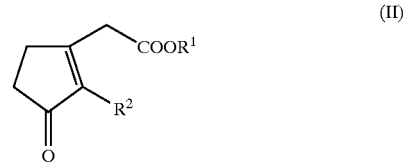

wherein R$^1$ represents a linear or branched C$_1$ to C$_4$ alkyl radical and R$^2$ represents a saturated or unsaturated, linear or branched, C$_1$ to C$_8$ hydrocarbon radical, the hydrogenation of which had proved impossible until our discovery of novel catalysts obtained by an original process.

The catalysts described in the above-mentioned patent application were obtained by a method which comprised treating equimolar amounts of an appropriate Ru(II) complex, for example, [(COD)Ru(2-methylallyl)$_2$] and a chelating diphosphine with an acid of formula HX, wherein X is a non-coordinating anion, said acid being used in a ratio not exceeding 2 molar equivalents per mole of the Ru(II) complex and the treatment being carried out in a non-coordinating or weakly coordinating medium, under an inert atmosphere.

Such catalysts were able to successfully hydrogenate substrates (formula II), amongst others, to provide their corresponding saturated homologues in strictly cis-configuration and with an enantiomeric excess of at least 60% in the (+)-1R-isomer. Such catalysts, and their use in asymmetric hydrogenation reactions, provided a breakthrough of outstanding importance for the single-step conversion of unsaturated substrates which had previously proved impossible to hydrogenate, into their saturated homologues. Moreover, their use in the conversion of substrates (formula II)-proved particularly valuable in the case of methyl 3-oxo-2-pentyl-1-cyclopentene-1-acetate, the asymmetric hydrogenation of which provided, in a single step, the preferred optically active isomer of methyl dihydrojasmonate or Hedione® (origin: Firmenich SA, Geneva, Switzerland), a well-known and widely used perfume ingredient.

In fact, amongst the four possible Hedione® stereoisomers, methyl (+)-(1R)-cis-3-oxo-2-pentyl-1-cyclopentaneacetate is known to develop at their best the odor characters, and namely the jasmine note, for which Hedione® is notorious, while the strength of this isomer's odor is also superior to that of the other isomers by several orders of magnitude. Therefore, the production of methyl (+)-(IR)-cis-3-oxo-2-pentyl-1-cyclopentaneacetate in an optically pure state, or of isomer mixtures which contain essentially this isomer, is of capital importance in the fragrance industry.

DESCRIPTION OF THE INVENTION

One object of the present invention is a ruthenium catalyst obtainable by a process which comprises putting into contact an appropriate Ru(II) complex, a chelating diphosphine and an acid comprising a non-coordinating anion, said Ru(II) complex and chelating diphosphine being present in equimolar amounts, the contact occurring in a non-coordinating or weakly coordinating medium and under an oxygen-free atmosphere, wherein the acid comprising the non-coordinating anion is used in an amount of about I molar equivalent per mole of the Ru(II) complex.

Reference to "about 1 molar equivalent of acid per mole of Ru(II) complex" signifies here a molar ratio between these two components which does not significantly differ from 1, and is preferably comprised within a range of between 0.95 and 1.10, more preferably from 1.0 to 1.10.

The above-mentioned catalysts of the invention provide surprisingly good results when used in the hydrogenation of substrates (II) in particular, but can also be conveniently used for the hydrogenation of substrates of general formula III

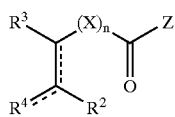

as defined in claim 12. Preferred embodiments of the hydrogenation process of the invention relate to the hydrogenation of substrates (formula III) having a carbon-carbon double bond in one of the positions indicated by the dotted lines which is at least trisubstituted, i.e. not more than one amongst the $R^2$, $R^3$ and $R^4$ groups represents hydrogen.

It will be apparent to the person skilled in the art from the disclosure which follows that the catalysts of the invention can also be successfully used in the hydrogenation of ethylenic bonds less sterically hindered than those of preferred substrates (formula III) described above. However, they are most advantageously used in the one-step conversion of the preferred substrates (formula III) defined above into their saturated homologues, as is apparent hereafter, particularly those wherein the double bond is tetrasubstituted.

We have in fact ascertained that the catalysts of the invention can be successfully and generally used in asymmetric hydrogenations and are able to readily hydrogenate di-, tri- and tetrasubstituted double bonds, isolated or occured in α,β- or β,γ-position to an ester function, in α,β-position to a ketone or aldehyde function and even in β,γ-position to an alcohol function, the ester and ketone groups being totally unaffected by the hydrogenation.

The catalysts of the invention comprise, or consist essentially of, the reaction product of the appropriate Ru(II) complex, the chelating diphosphine and the acid comprising the non-coordinating anion, the reaction occurring in a non-coordinating or weakly coordinating medium.

By an "appropriate Ru(II) complex" it is meant here any of the Ru(II) complexes currently known and used in the preparation of ruthenium catalysts, amongst which can be cited for example those wherein the metal is surrounded by dienyl and alkyl type ligands, such that the metal is σ-bonded to two of said ligands, which ligands further possess at least one bond π-bonded to the metal, two other coordination positions being π-bonded to the same said two ligands or to a distinct ligand.

Several ruthenium compounds are known from the prior art which comprise ligands fulfilling the above-mentioned conditions and which are convenient as precursors of the catalysts of the present invention.

One can cite more particularly, as appropriate ruthenium (II) complexes, the compounds of the [(diene)Ru(allyl)$_2$] type, wherein "diene" stands for example for COD (cycloocta-1,5-diene) or NBD (norbornadiene), or yet hepta-1,4-diene, and "allyl" represents an allyl or 2-methylallyl radical (see, for instance, J.-P. Genet et al., cited references; M. O. Albers et al., Inorganic Synth., 1989, 26, 249; R. R. Schrock et al., J. Chem. Soc. Dalton Trans., 1974, 951). Other appropriate ruthenium(II) complexes include the compounds of the [bis(pentadienyl)Ru] type, wherein "pentadienyl" stands for a pentadienyl, 2,4-dimethylpentadienyl, 2,3,4-trimethylpentadienyl, 2,4-di(tert-butyl)-pentadienyl or yet 2,4-dimethyl-1-oxapentadienyl radical (see, for example, R. D. Ernst et al., J. Organometallic Chem., 1991, 402, 17; L. Stahl et al., Organometallic 1983, 2, 1229; T. Schmidt et al., J. Chem. Soc. Chem. Commun., 1991, 1427; T. D. Newbound et al., Organometallics, 1990, 9, 2962).

Yet other appropriate Ru(II) complexes include [Ru(COD)(COT)], wherein COT stands for cycloocta-1,3,5-triene, [bis(2,4-cyclooctadienyl)Ru] and [bis(2,4-cycloheptadienyl)Ru] (see, for example, P. Pertici et al., J. Chem. Soc. Dalton Trans., 1980, 1961; Inorganic Synthesis 1983, 22, 176) and [Ru(NBD)(CHT)] wherein NBD is norbornadiene and CHT stands for cyclohepta-1,3,5-triene (see for example, H. Nagashima et al., J. Organometallic Chem. 1983, 258, C15).

Following a preferred embodiment of the catalysts of the invention, there is used as the Ru(II) precursor, the compound of formula: [(COD)Ru(2-methylallyl)$_2$], bis(2,4-dimethylpentadienyl)ruthenium (e.g. L. Stahl et al. or T. D. Newbound et al., references cited), bis(2,4-dimethyl-1-oxapentadienyl) ruthenium complexes (e.g. T. Schmidt et al., reference cited) or yet [Ru(COD)(COT)] (P. Pertici et al., ref. cited). [(COD)Ru(2-methylallyl)$_2$], the preparation of which was first reported by J. Powell et al., in J. Chem. Soc., (A), 1968, 159 (see also M. O. Albers et al., Inorganic Synthesis 1989, 26, 249, and [Ru(COD)(COT)] proved quite convenient from a practical point of view.

Amongst the chelating diphosphines which can be used as ligands in the catalysts of the invention, there can be cited as preferred embodiments those selected amongst the known chiral diphosphine or bis(phosphine) ligands which make it possible to obtain catalytic species convenient for homogeneous asymmetric hydrogenations. More particularly, such chiral diphosphines include those known under the abbreviations of Me-DuPHOS, Et-DuPHOS, BINAP, TolBINAP, SKEWPHOS, DIPAMP and CHIRAPHOS, the structures of which are represented hereafter for one of the enantiomers in particular, and wherein Ph stands for a phenyl group:

(R,R)-(+)-CHIRAPHOS (L1)

(R,R)-(+)-SKEWPHOS (L2)

-continued

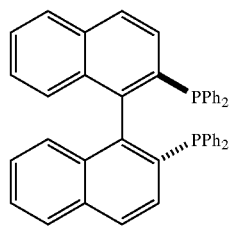

(L3)

(R)-(+)-BINAP

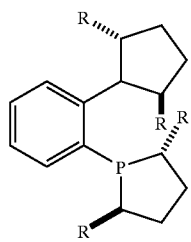

(L4)

R = Me: (R,R)-(-)-Me-DuPHOS
R = Et: (R,R)-(-)-Et-DuPHOS
R = Propyl: (R,R)-(-)-Pr-DuPHOS
R = iso-Propyl: (S,S)-(-)-iPr-DuPHOS

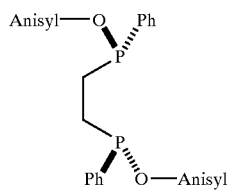

(L5)

Other chiral bidentate phosphines which can be used in the chiral catalysts of the invention include for instance those known under the name of NORPHOS, or yet the analogues of the DuPHOS type ligands, so-called "BPE", the structures of which are represented hereafter for one of the enantiomers.

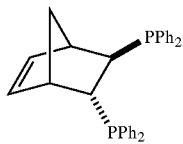

(L6)

(R,R)-(-)-NORPHOS

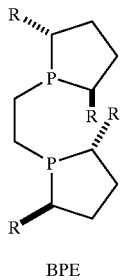

(L7)

BPE

R = alkyl radical from $C_1$ to $C_4$, linear or branched

All such ligands are either commercially available or can be prepared by methods previously reported in the literature.

Other particularly useful ligands for the preparation of the catalysts of the invention are the chiral diphosphines described for example in European patent applications nos. 564 406, 612 758 and 646 590, which disclose a large number of ligands appropriate for the catalysts according to the present invention. The contents of these documents, inasmuch as they relate to the definition and preparation or said chelating diphosphines, are hereby included by reference.

Amongst the chelating diphosphines described in EP 564 406, EP 612 758 and 646 590, it is preferred to use those obeying the general formula(L'8)

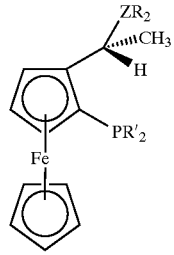

(L'8)

wherein Z is a phosphorus atom and R and R' are, independently from each other, a $C_1$ to $C_4$ alkyl group, linear or branched, a cyclohexyl group, a phenyl group or a phenyl group substituted by 1 to 3 alkyl groups having 1 to 4 carbons, the latter alkyl groups possibly being partially or totally fluorinated.

Even more preferred ligands of this type are those of formula

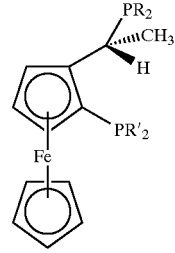

(L8)

R = tert-butyl, R' = phenyl
or R = R'=cyclohexyl
or R ≠ R'=cyclohexyl, phenyl
or R = m-tolyl, R' = phenyl
or R = cyclohexyl, R' = p-$CF_3$-phenyl and, more particularly, that known under the designation of (R)-(S)-JOSIPHOS (R=cyclohexyl, R'=phenyl) or (−)-JOSIPHOS, or yet its derivatives such as (R)-(S)-$CF_3$-JOSIPHOS.

Moreover, we also observed that the catalysts of the invention proved advantageous for the hydrogenation of many substrates, in particular those of formula (II), with a cis-stereoselectivity close to 100%, when they comprised in their structure both chiral and achiral chelating diphosphines. Thus, useful achiral ligands include for example the achiral or racemic ferrocenyl diphosphines represented hereafter:

(L9)

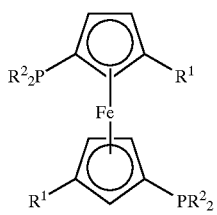

$R^1$ = alkyl radical from $C_1$ to $C_4$, linear or branched, or trimethysilyl
$R^2$ = alkyl radical from $C_1$ to $C_4$, linear or branched, or aryl or alkylaryl radical (L10)

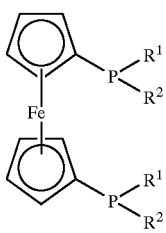

$R^1 \neq R^2$
$R^1$ = alkyl radical from $C_1$ to $C_4$, linear or branched, aryl radical or alkylaryl
$R^2$ = alkyl radical from $C_1$ to $C_4$, linear or branched, aryl or alkylaryl radical Other bidentate phosphines useful as ligands are represented below:

(L11)

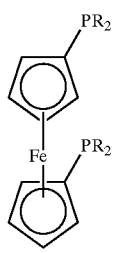

R represents an alkyl radical from C1 to C4, linear or branched, an aryl radical or an alkylaryl radical (L12)

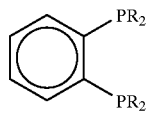

R has the meaning indicated for (L11)

(L13)

$R_2P-(CH_2)_{\overline{n}}-PR_2$ n = 0 to 4
R = cyclopentyl, cyclohexyl or phenyl In the context of the invention, there can yet be cited the optically active diphosphines of formula (L14)

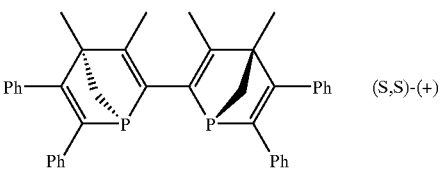

(L14)

(S,S)-(+)

as well as the corresponding racemic mixtures of isomers, reported in International patent application WO 96/20202. The contents of the latter related to the preparation of such ligands are hereby included by reference.

In a general manner, there can be used as ligands in the catalysts of the invention any chelating diphosphines comprising substituent groups capable of rendering the diphosphine sufficiently electron-rich to allow it to stabilize the metal, without however depriving said metal of its ability to coordinate the substrate to be hydrogenated and more particularly substrates of formula (II) and (III) mentioned above, the asymmetric hydrogenation of which had proved heretofore notoriously difficult, if not impossible.

It has also been observed that the diphosphines having a certain number of alkyl or cycloalkyl type substituents revealed themselves particularly useful for the aim of the invention and provided catalysts which were very active and efficient for the hydrogenation of substrates of formula (II) and (III).

It is apparent from the above that the preferred ligands for preparing the catalysts of the invention are diphosphine ligands in which the two phosphorous atoms are bridged by groups of the alkyl, 1,2-benzenyl, bis(naphthalenyl) or yet 1,1'-ferrocenyl type, optionally substituted, said phosphorous atoms further carrying two other substituents, which can be identical or different and formed of alkyl, aryl or alkylaryl radicals, or yet alicyclic radicals.

However, it is impossible to exhaustively illustrate here all the ligands which can be used in the catalysts of the invention and many other chelating diphosphines, not specifically cited above, or not falling under the above definitions, prove useful for the aim of the latter. The examples given illustrate preferred embodiments which are not to be interpreted as restricting the scope of the invention, inasmuch as the person skilled in the art is well able, without particular effort and using her general knowledge to select such ligands so as to achieve the aim described. To this effect, the skilled person can also find inspiration in the many prior art references, namely those cited in this description, to select many such ligands which, when used according to the invention here-described, make it possible to obtain catalysts able to achieve the same effect, i.e. hydrogenate substrates of formula (II) and (III) with essentially cis-stereo-selectivity (90% or more) for (formula II) and providing, where applicable, an excess of at least 60% in one of the cis-enantiomers.

The catalysts of the invention which comprise diphosphine ligands of the DuPHOS, BINAP, ToIBINAP, SKEWPHOS or JOSIPHOS type are particularly advantageous as catalysts for the asymmetric hydrogenation of the substrates of formula (If) and (III).

Amongst the latter catalysts, those which comprise ligands of the SKEWPHOS, JOSIPHOS or Me-DuPHOS type, and preferably of the two latter types, showed themselves capable of particularly advantageous performances and are therefore preferred according to the invention. (R,R)-(−)-Me-DuPHOS, or (−)-1,2-bis(2,5-dimethylphospholano)benzene, and (R)-(S)-JOSIPHOS or (R)-(S)-

CF$_3$-JOSIPHOS, made it possible to obtain choice catalysts according to the invention.

The ligands having formula L1 to L14 represented below are either commercially available compounds or they can be prepared according to processes analogous to previously described methods.

For example, the ligands of the DuPHOS, SKEWPHOS, BINAP, CHIRAPHOS, DIPAMP and NORPHOS type are mostly commercial products and, in any event, they can be obtained via processes described in the literature, namely in reference works such as the books of R Noyori, Asymmetric Catalysis in Organic Synthesis, John Wiley & Sons, N.Y. (1994), Chap. II and J. Ojima, Catalytic Asymmetric Synthesis, VCH Publishers, N.Y. (1994), Chap. 1, and the original references there-cited wherein such ligands were first reported.

The ligands of formula (L7) can be prepared as described for example in U.S. Pat. No. 5,171,892.

The ligands of formula (L8) and (L'8) can be prepared as described in the references already cited (see also A. Togni et al., J. Amer. Chem. Soc. 1994, 116, 4062) and some of them are commercially available (Rcyclohexyl, R'=phenyl for example; origin: STREM Chemicals, Inc.).

The ferrocenyl ligands of formula (L9), (L10) or (L11), when not available commercially, can be prepared by methods analogous to those reported in the literature (see, for example, I.R. Butter et al., Synth. React. lnorg. Met.-Org. Chem., 1985, 15, 109; M.D. Rausch et al., J. Organometallic Chem., 1967, 10, 127; R.A. Brown et al., Polyhedron 1992, 20, 2611; G. Herberich et al., Chem. Ber., 1995, 128, 689) starting from ferrocene and according to the following reaction schemes:

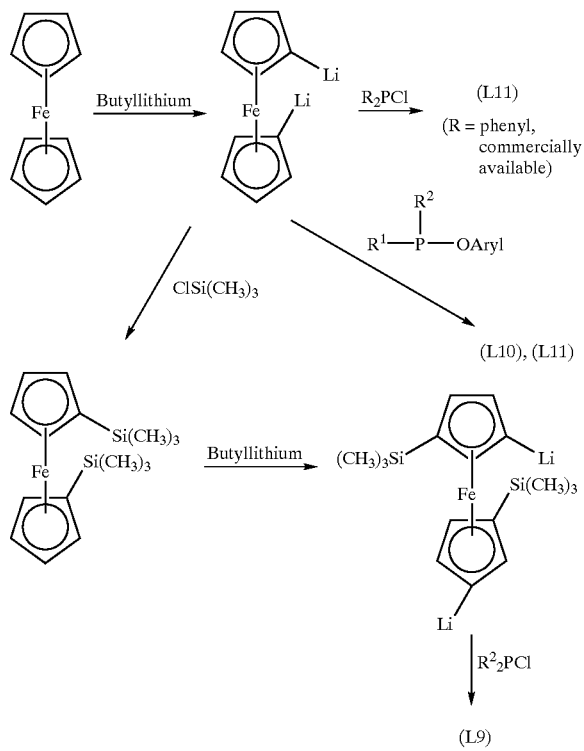

The (L12) and (L13) ligands are quite common and many are commercialized. Amongst the (L13) ligands, those wherein n=0 can be prepared by a variety of known methods (see, for example, R. Appel et al., Chem. Ber., 1975, 108, 1783 and references cited therein; M. Baudler et al., Chem. Ber. 1972, 105, 3844; K. Issleib et al., Journal fiir Praktischc Chemie, 1969, 311, 463).

The non-coordinating anion to be used in the catalysts of the invention can be a base conjugate of a variety of strong acids and includes for example the anions selected from the group consisting of $BF_4^-$, $PF_6^-$, $SbF_6^-$, $AsF_6^-$ and $B[3,5-(CF_3)_2C_6H_4]_4^-$. Thus, suitable acids that contain this conjugate anion include, amongst others, those of formula $RBF_4$, $RPF_6$, $RSbF_6$, $RAsF_6$, and $RB[3,5-(CF_3)_2C_6H_4]_4$ wherein R represents hydrogen or a $(C_6H_5)_3C$ group.

According to a preferred embodiment of the invention, the non-coordinating anion is a base conjugate of an acid of formula H-Anion, wherein the anion is selected amongst the anions $BF_4^-$, $PF_6^-$, $SbF_6^-$, $AsF_6^-$, or yet $HB[3,5-CF_3)_2C_6H_4]_4^-$. Such acids are typically used in the form of the corresponding etherates (for example $HBF_4.R_2O$, $R=CH_3$ or $C_2H_5$) or of any other onium type salt (phosphonium for example). These etherates are commercial products, or they can be prepared from the corresponding silver salts, by reacting with HCl. In the latter case, the silver salt, for example $AgBF_4$, $AgPF_6$, $AgSbF_6$ or $AgAsF_6$ will be typically reacted with HCl, in a solvent containing a dialkylether, for example a mixture of dicholormethane and diethylether. As the silver chloride precipitates, it provides the etherate solution of the acid, which can then be used according to the invention in the reaction with the ruthenium complex and the phosphine ligand.

Amongst the above-mentioned H-Anion acids, wherein the anion represents the non-coordinating anion, tetrafluoroboric acid is preferred and typically used in the form of its etherate, as commercially available in glass or plastic vials. If necessary, this product is titrated to ensure that the concentration of acid is about 1 molar equivalent of the molar amount of Ru complex.

The reaction according to which the catalyst of the invention can be obtained occurs in a non-coordinating or weakly coordinating medium and under an oxygen-free atmosphere. By an "oxygen-free atmosphere" it is meant here an atmosphere whose oxygen content is lower than 200 ppm, and preferably not above 5 to 10 ppm.

By the "non-coordinating or weakly coordinating medium" it is typically meant here a non-coordinating or weakly coordinating solvent. Examples of suitable solvents include esters, ketones, aliphatic, acyclic or cyclic hydrocarbons, chlorinated hydrocarbons and ethers, as long as they have no capability to strongly coordinate the ruthenium. Specific examples include dichloromethane, dichloroethane, ethyl pivalate, methyl acetate, ethyl acetate, isopropyl acetate, acetone, 2-butanone, 3-pentanone, hexane, heptane, cyclohexane, cycloheptane and methyl tert-butyl ether.

According to a preferred embodiment, dichloromethane or a mixture of it with other, non-coordinating or weakly coordinating solvents, in particular those mentioned above, is used.

It should be noted that the use of the strongly coordinating or protic solvents current in the art for the preparation of Ru catalysts, provided species which were inactive or inadequate for the hydrogenation of the substrates of formula (II) or (III) previously mentioned.

The non-coordinating or weakly coordinating medium may also consist of a mixture of a solvent such as described above with a substrate of formula (II) or (III), or even essentially ofjust said substrate of formula (II) or (III).

Thus, according to an embodiment of the invention there is provided a catalyst obtainable in the presence of an organic non-coordinating or weakly coordinating solvent and/or of a substrate of formula

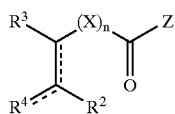

having a double bond in one of the positions indicated by the dotted lines and wherein
  a) n=0 and Y represents hydrogen, a $C_1$ to $C_4$ linear or branched alkyl radical or an $OR^1$ group, $R^1$ standing for a linear or branched lower alkyl radical; or
  b) n=1, X represents a $CH_2$ group and Z stands for an $OR^1$ group wherein $R^1$ has the meaning cited in a); or
  c) n=1, X represents an oxygen atom and Z represents a $C_1$ to $C_4$ linear or branched alkyl radical, or X represents a $NR^5$ group, $R^5$ standing for a lower alkyl radical, and Z stands for a linear or branched $C_1$ to $C_4$ alkyl radical;
and wherein
  $R^2$ represents hydrogen or a saturated or unsaturated, linear or branched $C_1$ to $C_8$ radical derived from a hydrocarbon;
  $R^3$ and $R^4$ are taken separately and each represents hydrogen or a saturated or unsaturated, linear or branched $C_1$ to $C_8$ radical derived from a hydrocarbon, or are taken together to form a five-membered or six-membered ring which also contains the carbon atoms of the ethylenic bond.

Preferred substrates of the invention are compounds of formula (III) wherein not more than one of the $R^2$, $R^3$ and $R^4$ symbols represents hydrogen.

By a lower alkyl radical it is meant here a $C_1$ to $C_4$, linear or branched alkyl radical.

When the catalyst of the invention is obtained in the presence of the 20 substrate, preferred embodiments of said catalyst include the presence of substrates formed of compounds of formula(II)

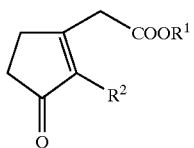

(II)

wherein $R^1$ is a linear or branched alkyl radical from $C_1$ to $C_4$ and $R^2$ is a saturated or unsaturated, linear or branched, $C_1$ to $C_8$ hydrocarbon radical,
or of formula

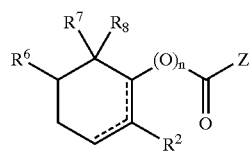

having a double bond in one of the positions indicated by the dotted lines and wherein:
  a) n=0 and Z represents an $OR^1$ group, $R^1$ standing for a $C_1$ to $C_4$ linear or branched alkyl radical;
or
  b) n=1, and Z represents a $C_1$ to $C_4$ linear or branched alkyl radical; and wherein $R^2$ is a saturated or unsaturated, linear or branched, $C_1$ to $C_8$ hydrocarbon rest and $R^6$, $R^7$ and $R^8$ represent each hydrogen or a lower alkyl radical of $C_1$ to $C_4$.

In this context, particularly useful catalysts are those wherein the substrate present in the reaction medium is a compound of formula (IV) in which n=0 and Y represents a $OR^1$ group wherein $R^1$ represents a methyl or ethyl group, $R^2$ represents a methyl radical and $R^6$, $R^7$ and $R^8$ are identical or different and represent each hydrogen or a methyl group.

More preferred substrates are methyl 3-oxo-2-pentyl-1-cyclopentene-1-acetate and methyl 2,6,6-trimethyl-2-cyclohexene-1-carboxylate, which, as will become apparent shortly, make it possible to obtain preferred isomers of useful perfume ingredients, amongst which Hedione®.

As previously mentioned, the medium in which the reaction takes place can also be a mixture of one of the substrates mentioned above and a non-coordinating or weakly coordinating solvent, in which case the latter will be preferably chosen amongst the solvents already cited above, and more preferably as a solvent comprising dichloromethane.

The catalysts of the invention described above are extremely active species which have been found to improve upon those described in the WO 97/18894 patent application. In fact, although the catalysts described in the above document are quite appropriate for the hydrogenation of the same type of ethylenic bonds and substrates as are here contemplated, we have now unexpectedly discovered that complete conversion of these substrates can now be obtained, by means of the presently claimed catalysts, in even shorter reaction times, while using lower amounts of catalyst.

Amongst the catalysts of the invention described above, particularly effective species for the asynmnetric hydrogenation of methyl 3-oxo-2-pentyl-1-cyclopentene-1-acetate were those wherein the Ru(II) complex is $[(COD)Ru(2$-methylallyl)$_2]$ and the anion $BF_4^-$ derived from $HBF_4$.etherate, and wherein (R,R)-(−)-Me-DuPHOS or (R)-(S)-JOSIPHOS was used in a medium comprising dichloromethane, in both cases preferably in the presence of the substrate mentioned here-above.

The invention further realizes a process for the preparation of a ruthenium catalyst, characterized in that an appropriate Ru(II) complex and a chelating diphosphine present in equimolar amounts, and an acid comprising a non-coordinating anion, are reacted under an oxygen-free atmosphere and in a non-coordinating or weakly coordinating medium, wherein the acid comprising the non-coordinating anion is used in an amount of about 1 molar equivalent per mole of the Ru(II) complex.

The nature of the parameters of this process, i.e. the Ru(II) complex, the chelating diphosphine, the non-coordinating anion and the reaction medium, have been described in detail above.

According to the invention, the preparation of the catalyst can be carried out at room temperature or at a lower temperature. Higher temperatures may also be used, and can be chosen such as not to influence the catalyst's properties and its efficiency in the hydrogenation of the substrates. Nevertheless, the application of room temperature proves to be advantageous from a practical point of view.

As mentioned before, the catalyst is prepared under inert, oxygen-free atmosphere, typically under argon or nitrogen.

Preferred embodiments of this process correspond to the use of the preferred parameters already described above with regard to the catalysts, e.g. the use of optically active diphosphines, preferred anions and so on.

In particular, the preparation of the catalyst in a medium consisting of a non-coordinating or weakly coordinating solvent and a small amount of substrate, in particular substrates of formula (II) or (IV), turns out to be a very advantageous embodiment of the process of the invention.

The catalysts according to the present invention which have been prepared like this are obtained as solutions, in the solvent and the substrate, of the product which is the result of the reaction of the Ru(II) complex with the diphosphine ligand and the acid from which the anion is derived. These catalytic solutions may be used as such for the asymmetric hydrogenation of the substrates, namely compounds of formula (II) and (IV). They can be kept under an oxygen-free atmosphere and will stay active for several days.

Catalytic solutions according to the present invention are thus obtained, having a variable concentration in the catalyst of the invention, for example of the order of 0.04 to 0.07 M (0.04 to 0.07 mmoles of catalyst/ml of catalytic solution), and more preferably of the order of 0.055 M, which proved to be very advantageous for the hydrogenation of substrates of formula (I) and (IV) in particular.

Preferred pre-catalysts of the invention are those of formula (V)

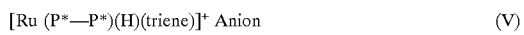  (V)

wherein P*—P* represents a chelating bis(phosphine) ligand, possibly chiral, X represents a non-coordinating anion and "triene" stands for cyclohepta-1,3,5-triene, cycloocta-1,3,5-triene or a similar species. These most preferred compounds require the presence of at least one COD molecule in the precursor ruthenium (II) complex. According to a preferred embodiment of this catalyst, the diphosphine is (R,R)-(−)-Me-DuPHOS or (R)-(S)-JOSIPHOS and the anion is $BF_4^-$.

Other embodiments of this catalyst are apparent from the text above, the diphosphine ligand and the anion being varied at will, having the meaning previously defined and being specifically cited above with regard to particular examples of the catalysts of the invention.

The preparation of preferred embodiments of the catalysts of formula (V) are described in detail further on.

The ruthenium catalysts of the invention are useful for the hydrogenation, optionally asymmnetric, of carbon-carbon double bonds in general and more particularly highly sterically hindered ones.

Their activity with regard to the hydrogenation of the substrates of formula (II), (III) and (IV) in particular is excellent, unlike what is the case of the prior art ruthenium catalysts. They enable the preparation of the saturated compounds corresponding to substrates of formula (II) and (IV) with a cis-stereoselectivity above 95% and, in most cases of the order of 98% or more. When chiral chelating bis (phosphines) are present in the structure of the catalysts of the invention, the asymmetric hydrogenation of the above-mentioned substrates provides enantiomers with at least 60% e.e., and in many cases above 85% ee.

According to preferred embodiments of the invention, there are thus also provided processes for the preparation of compounds resulting from the hydrogenation of compounds of formula (II) and (IV).

Therefore, the invention also relates to a process for the preparation of a compound of formula

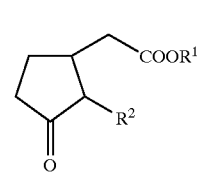  (I)

wherein $R^1$ is a linear of branched $C_1$ to $C_4$ alkyl radical and $R^2$ is a saturated or unsaturated, linear or branched $C_1$ to $C_8$ hydrocarbon rest, essentially in the form of an isomer of cis-configuration, characterized in that a substrate of formula

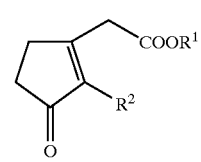  (II)

in which $R^1$ and $R^2$ have the meaning indicated above, is hydrogenated in the presence of a Ru catalyst as previously described and at a hydrogen pressure comprised between atmospheric pressure and 500 bar ($5 \times 10^7$ Pa).

Another object of the invention is a process for the preparation of a compound of formula

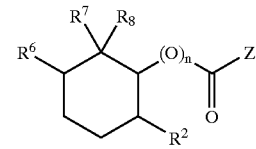

wherein the dotted lines and the symbols n, Z, $R^2$, $R^6$, $R^7$ and $R^8$ are defined as in formula (IV), essentially in the form of an isomer of cis-configuration, characterized in that a substrate of formula (IV) as defined above is hydrogenated in the presence of a ruthenium catalyst according to the invention and at a hydrogen pressure comprised between atmospheric pressure and 500 bar.

Preferred embodiments of these two processes resort to the use of catalysts which comprise appropriate chiral chelating diphosphines, such as to provide the compound of formula (I) or (VI) essentially in the form of an optically active isomer of cis-configuration.

As is current in the art, the substrate is preferably used in a pure state and free of oxygen.

The hydrogenation reaction can be carried out in a non-coordinating or weakly coordinating solvent, the latter being defined as already described above. Specific examples thus include dichloromethane, dichloroethane, ethyl pivalate, methyl acetate, ethyl acetate, isopropyl acetate, acetone, 2-butanone, 3-pentanone, hexane, heptane, cyclohexane, cycloheptane and methyl tert-butyl ether, and their mixtures. The use of a solvent comprising dichloromethane is preferred.

Alternatively, the hydrogenation medium in which the reaction takes place may consist essentially of the substrate, or be highly concentrated in the latter.

According to a preferred embodiment of the hydrogenation process of the invention, the catalyst is generated in situ before the hydrogenation of the substrate, or in the presence of a small amount of the latter.

All the racemic or achiral ligands previously cited can be used to generate catalysts which make it possible to prepare the compounds of formula (I) or (VI) essentially in the form of the cis-configuration isomer, whereas the optically active chelating diphosphines provide the desired optically active cis form of the cited compounds of formula (I) or (VI).

Of course, racemic ligands can be subjected to separation, for example by means of chiral columns, to provide the corresponding enantiomers.

Following a particularly preferred embodiment of the hydrogenation process according to the present invention, methyl 3-oxo-2-pentyl-1-cyclopentene-1-acetate is used as the substrate, in order to obtain Hedione® in the form of the preferred cis- and (+)-cis-configuration isomers.

The catalysts according to the present invention which start from the [(COD)Ru(2-methylallyl)$_2$] precursor and have ligands of the DuPHOS type, and in particular Me-DuPHOS, have proved to be particularly useful for the hydrogenation of this substrate, carried out in a solvent of dichloromethane.

Other preferred conditions for the hydrogenation of this substrate include the use of a catalyst comprising [(COD)Ru(2-methylallyl)$_2$] and (R)-(S)-JOSIPHOS as the ligand, in a hydrogenation medium comprising a hydrocarbon such as hexane, heptane or their saturated cyclic analogues, and more preferably methyl tert-butyl ether.

This latter preferred embodiment of the hydrogenation process of the invention makes it possible to obtain (+)-cis-Hedione® with an enantiomeric excess of 80% or more. Still another preferred embodiment resorts to the use of [Ru(COD)(COT)] and (R)-(S)-JOSIPHOS.

The hydrogenation can be carried out at pressures from about atmospheric pressure to 500 bar (5×10$^7$ Pa). Pressure values comprised between 20, and more preferably 50 to 200 bar or even higher are quite convenient.

The reaction may take place at temperatures of up to 50 to 60° C., or even 100° C. Preferably, one will work at room temperature or even a lower temperature. It has been found for example that temperatures down to −10° C., or even lower, made it possible to obtain good results.

The molar concentrations in which these catalysts may be typically used can go up to 4 molar %, relative to the substrate, but preferred embodiments of the hydrogenation process of the invention comprise using the catalyst in a molar concentration of about 0.01 to 1%, more preferably between 0.01 and 0.5 molar %. Excellent results could be systematically obtained with concentrations of 0.02 to 0.1%, more particularly 0.025 to 0.05 molar %, relative to the substrate.

Moreover, it has also been found that it is advisable to use solutions in which the substrate is concentrated, and the best results have been obtained when the concentration of the substrate in the hydrogenation medium was from about 0.4 to 1.5 molar with respect to the volume of this medium.

To hydrogenate the reaction mixture, the latter is pressurized under hydrogen in a conventional manner and as is described in the examples below. With the catalysts of the invention, used in concentrations of the order of 0.05 molar % relative to the substrate complete conversion of the latter could be obtained in less than 24 h, and in the best cases in 6 hours or less.

The invention will now be described in greater detail by way of the following examples, wherein the temperatures are indicated in degrees Celsius and the abbreviations have the usual meaning in the art.

These examples illustrate particular and best embodiments of the invention, many variations of which can be readily construed from the description above. Namely, in the many examples of catalysts taught in the WO 97/18894 application, which resulted from the various combinations of the preparation parameters also described in detail in the preceding pages of the instant disclosure, the use of about 1 molar equivalent of acid comprising a non-coordinating anion per mole of Ru(II) complex, as instantly taught, provided enhanced novel catalysts. The contents of this WO 97/18894 application is therefore hereby included by reference, to the extent that it provides specific examples of the many catalysts that can be obtained by varying the nature of the Ru(II) complex precursor, of the diphosphine ligand, of the non-coordinating anions and their precursors, and of the non-coordinating or weakly-coordinating solvent.

It is to be appreciated that the use of the respective enantiomers of the ligands mentioned throughout this specification, for example of (S,S)-(+)-MeDuPHOS or (S)-(R)-JOSIPHOS, makes it possible to obtain the corresponding enantiomers of compounds of formula (I) and (VI) mentioned above.

In the examples hereafter, reference to a "glovebox" means a glovebox under Ar or nitrogen and the oxygen content of which is under 10 ppm.

EXAMPLE 1

Preparation of [Ru((R,R)-Me-DuPHOS)(H)(COT)](BF$_4$)

In a glovebox, there were charged into a 50 ml flask 260.7 mg (0.816 mmole) of [(COD)Ru(methylallyl)$_2$] (origin: Acros Organics) and 10.8 ml of methylacetate. A separate 10 ml vial was charged with 250 mg (0.816 numole) of (R,R)-(−)-Me-DuPHOS (origin: STREM Chemicals), 5 ml of CH$_2$Cl$_2$ and 137 μl of 81% HBF$_4$.etherate (0.816 mmole of HBF$_4$). The contents of this 10 ml vial were then poured into the stirred mixture contained in the 50 ml flask and this mixture was further stirred during 12 hours. A yellow precipitate was collected by filtration (180 mg, 0.299 mmole, yield: 37%), consisting of [Ru((R,R)-Me-DuPHOS)(H)(COT)]$^+$BF$_4^-$ which was extensively analyzed by spectroscopy. The structure of this crystalline product was unambiguously established by spectroscopic analysis. The data obtained were the following ($^1$H and $^{13}$C NMR established relative to trimethylsilane; CI=Chemical Ionisation):

$^1$H NMR(CD$_2$Cl$_2$) δ 7.58(m, 4H); 6.57(t, J=8.4 Hz, 1H); 6.30(dd, J$_1$=6.4 Hz, J$_2$=8.9 Hz, 1H); 5.62(m, 2H); 5.37(q, J=8.4 Hz, 1H); 5.26(t, J=7.9 Hz, 1H); 2.71(m, 2H); 2.55–2.15(m, 5H); 1.33(dd, J$_1$=6.9 Hz, J$_2$=17.2 Hz, 3H); 1.30(m, 1H); 1.13(dd, J$_1$=6.9 Hz, J$_2$=17.2 Hz, 3H); 0.93(dd, J$_1$=6.9 Hz, J$_2$=17.2 Hz, 3H); 0.70(dd, J$_1$=6.9 Hz, J$_2$=17.2 Hz, 3H); −9.94(t, J=29 Hz, 1H).

$^{13}$C($^1$H) NMR (CD$_2$Cl$_2$) δ 141.2(m, C), 141.0(m, C), 132.0(d, J$_{pc}$=14 Hz, CH), 131.5(d, J$_{pc}$=14 Hz, CH), 131.3(s, CH), 131.0(s, CH), 102.3(s, CH), 101.2(s, CH), 99.2(s, CH), 96.2(s, CH), 94.3(s, CH), 94.3(s, CH), 44.5(d, J$_{pc}$=38 Hz, CH), 44.4(d, J$_{pc}$=14 Hz, CH), 40.9(d, J$_{pc}$=32 Hz, CH), 40.1(d, J$_{pc}$=24 Hz, CH), 37.5(s, CH$_2$), 37.4(s, CH$_2$), 36.4(s, CH$_2$), 35.9(s, CH$_2$), 34.8(s, CH$_2$), 32.0(s, CH$_2$), 18.3(s, CH$_3$), 16.2(d, J$_{pc}$=6.0 Hz, CH$_3$), 14.4(s, CH$_3$), 12.6(s, CH$_3$);

$^{19}$F NMR (CD$_2$Cl$_2$) δ 10.5 (relative to C$_6$F$_6$);

$^{31}$P NMR (CD$_2$Cl$_2$) δ 87.5 (d, J$_{pp}$=20.0 Hz), 84.9 (d, Jpp=20.0 Hz) (relative to 85% aqueous H$_3$PO$_4$);

MS (CI) 515, 339, 287, 231, 209, 193, 180.

The identity of this compound was also ascertained by mass spectrometry, $^1$H, $^{13}$C, $^{19}$F, $^{31}$P NMR spectroscopy, DEPT and $^1$H - $^1$H, $^1$H - $^{13}$C correlations. The mass spectrum gives a molecular ion for the cationic portion of this complex at 515 m/e. The $^{19}$F NMR spectrum displays a single resonance for a $BF_4^-$ moiety indicating the existence of one species. The $^{31}P$ NMR spectrum displays two doublets consistent with one species containing one DuPHOS ligand with inequivalent phosphorous atoms. The $^1H$ NMR spectrum clearly indicates the presence of a hydride bound to ruthenium, coupled to two phosphorous atoms at −9.94 ppm. Further, there are six resonances for the CH protons on the cyclooctatriene ligand (which was also supported by a $^1H$-$^{13}C$ correlation). $^{13}C$ ($^1H$) and DEPT experiments are also consistent with this structure. There are six resonances for the cyclooctatriene ligand between 103 and 94 ppm indicating the alkenyl nature of this ligand. The methylene groups on the COT ligand were assigned and are at 35.9 and 32.0 ppm. Further, all remaining $^{13}C$ resonances are consistent with a single DuPHOS ligand attached to ruthenium. Finally, the structure of the precatalyst mentioned above was also confirmed by X-ray analysis.

The concentration of the commercial $HBF_4$.etherate in $HBF_4$ could be carefully monitored before its use, according to the following method.

In a glovebox, a 10 ml glass vial was charged with 20.0 mg (0.050 mmole) of $(Ph)_2PCH_2CH_2P(Ph_2)$ (origin: STREM Chemicals) and 500 μl of $CH_2Cl_2$. To this solution there were added 500 μl of an approximately 0.1 M solution of $HBF_4$.etherate/$CH_2Cl_2$. The solution was placed in a NMR tube, sealed and placed in a NMR probe at −70° C. A $^{31}P$-proton coupled spectrun was collected and integrated. By comparing the integral of free $(Ph)_2PCH_2Cli_2P(PH_2)$ with the resonances of the protonated diphosphine a true value for the titre of the $HBF_4$.etherate/$CH_2Cl_2$ was obtained.

The title compound was also obtained using [Ru(COD)(COT)] as the starting ruthenium complex.

EXAMPLE 2

Hydrogenation of Methyl 3-oxo-2-pentyl-1-cyclopentene-1-acetate

In a glovebox, into a 10 ml glass vial were placed 15.5 mg (0.0485 mmole) of [(COD)Ru(2-methylallyl)$_2$], 14.9 mg (0.0485 mmole) of (R,R)-Me-DuPHOS and 250 μl of methyl 3-oxo-2-pentyl-1-cyclopentene-1-acetate (1.08 nmuole). To this suspension was added 0.630 ml of a 0.081 M solution of titrated $HBF_4$.etherate (0.049 nunole) in $CH_2Cl_2$ with stirring. This concentrated solution was stirred for 1.5 hours, after which 21.5 g (95.9 mmole) of methyl 3-oxo-2-pentyl-1-cyclopentene-1-acetate and 11.5 ml of $CH_2Cl_2$ were added. The resulting yellow solution was placed in a 75 ml autoclave, purged with hydrogen and pressurized to 90 bar of hydrogen. After 8 hours, the solution was exposed to air and passed through a column of silica gel to separate the catalyst. This gave a 99% yield of the desired Hedione® product with the following ratios of isomers: cis/trans=98/2; (+)-cis/(−)-cis=82.4/17.6, 64.8% ee.

As prepared above, the catalyst of the invention was present in the reaction medium in 0.05 molar % relative to methyl 3-oxo-2-pentyl-1-cyclopentene-1-acetate.

A similar procedure, but adding methyl 3-oxo-2-pentyl-1-cyclopentene-1-acetate neat, provided a 99% yield of the desired Hedione® product with the following ratios of isomers: cis/trans=98/2; (+)-cis/(−)-cis=83.4/16.6, 66.8% ec.

EXAMPLE 3

Hydrogenation of Methyl 3-oxo-2-pentyl-1-cyclopentene-1-acetate using the Catalyst Described in Example 1

In a glovebox, into a 10 ml glass vial were placed 15.0 mg (0.0250 mmole) of [((R,R)-Me-Duphos)Ru(H)(cyclooctatriene)]$BF_4$, 5.62 ml of $CH_2Cl_2$ and 11.23 g (50.0 mmole) of methyl 3-oxo-2-pentyl-1-cyclopentene-1-acetate. The resulting yellow solution was placed in a 75 ml autoclave, purged with hydrogen and pressurized to 90 bar of hydrogen. After 6 hours, the solution was exposed to air and passed through a column of silica gel to separate the catalyst. This gave a 99% yield of the desired Hedione® product with the following ratios of isomers: cis/trans=98/2; (+)-cis/(−)-cis=82.3/17.7, 64.6% ee.

Using in the above-described process 7.5 mg of catalyst (0.0125 mmole) provided a final product with the same characteristics as above, in 98% yield, after 33 h of reaction.

COMPARATIVE EXAMPLE 1

Hydrogenation of Methyl 3-oxo-2-pentyl-1-cyclopentene-1-acetate

Proceeding in a similar manner to that described in Example 2, but in the presence of a catalyst prepared according to the process described in WO 97/18894, i.e. using equimolar amounts of [(COD)Ru(2-methylallyl)$_2$] and diphosphine ligand (see table below), HBF4 . etherate in an amount of 2 molar equivalents per mole of [(COD)Ru(2-methylallyl)$_2$], in dichloromethane or a mixture of the latter with other solvents (see table), ethyl 3-oxo-2-pentyl-1-cyclopentene-1-acetate was hydrogenated under a variety of conditions as detailed in the table below, to providc Hedione® in the form of a variety of products as cited in the table. The molar concentration of the substrate in the hydrogenation medium was always approximately the same to avoid dilution effects.

TABLE I

| Ligand | Hydrogenation | Acid solvent | Molar % of catalyst relative to substrate | $H_2$ pressure ($10^6$ Pa) | Reaction time h | Substrate conversion % | cis/ trans ratio | (+)-cis/ (−)-cis ratio |
|---|---|---|---|---|---|---|---|---|
| (R,R)-Me-DuPHOS | $CH_2Cl_2$ | $CH_2Cl_2$ | 2 | 9 | 0.5 | 99 | 97:3 | 80:20 |
| (R,R)-Me-DuPHOS | $CH_2Cl_2$ | $CH_2Cl_2$ | 1 | 9 | 1.5 | 99 | 98:2 | 80:20 |
| (R,R)-Me-DuPHOS | $CH_2Cl_2$ | $CH_2Cl_2$ | 0.5 | 9 | 20 | 99 | 97:3 | 80:20 |
| (R,R)-Me-DuPHOS | $CH_2Cl_2$ | $CH_2Cl_2$ | 0.3 | 5 | 70 | 99 | 99:1 | 84:16 |
| (R)-(S)-JOSIPHOS | hexane | $CH_2Cl_2$ | 0.2 | 3.5 | 20 | 99 | 98:2 | 93:7 |
| (R)-(S)-JOSIPHOS | hexane | $CH_2Cl_2$ | 0.1 | 4 | 18 | 98 | 72:28 | 90:10 |
| (R)-(S)-JOSIPHOS | MTBE* | $CH_2Cl_2$ | 0.1 | 4 | 20 | 98 | 96:4 | 89:11 |
| (R)-(S)-JOSIPHOS | isopropyl ether | $CH_2Cl_2$ | 0.1 | 4 | 18 | 98 | 97:3 | 89:11 |
| (R)-(S)-JOSIPHOS | cyclohexane | $CH_2Cl_2$ | 0.2 | 3.5 | 20 | 96 | 98:2 | 93:7 |
| (R)-(S)-JOSIPHOS | heptane | $CH_2Cl_2$ | 0.1 | 4 | 18 | 97 | 80:20 | 90:10 |

*methyl tert-butyl ether

It appears clearly from this table that far longer reaction times are needed with the method described in WO 97/18894 to obtain full conversion of the substrate, when the catalyst containing (R,R)-MeDuPHOS is used in a molar concentration below 0.3%, whereas with the corresponding catalysts of the instant invention the conversion can be complete in 6 h even when the catalyst is used at 0.05 molar % relative to the substrate.

COMPARATIVE EXAMPLE 2

Hydrogenation of Methyl 2,6,6-trimethyl-1-cyclohexene-1-carboxylate

Proceeding as described in WO 97/18894 and in comparative Example 1, the above substrate was hydrogenated at a pressure close to 100 bar ($10^7$ Pa) and at room temperature, using a catalyst which comprised a variety of ligands, as indicated in the table hereafter. In all the trials, 2 molar equivalents of $HBF_4$.etherate were used per mole of [(COD)Ru(2methylallyl)$_2$] and the catalysts thus obtained were employed at 2 molar % concentration with respect to the substrate. The conversion rates, and the isomer characteristics of the methyl (1S,2S)-2,2,6-trimethyl-1-cyclohexane-carboxylate obtained are indicated in Table 2 hereafter:

TABLE II

| Ligand | Reaction time h | Substrate conversion % | Cis/trans ratio | Enantiomeric excess in (1S,2S)-isomer % |
|---|---|---|---|---|
| (S)-TolBINAP | 24 | 96 | 99:1 | 84 |
| (R)-TolBINAP | 21 | 96 | 99:1 | 85 |
| (−)-MeDuPHOS | 21 | 98 | 99:1 | 58 |
| (S)-BINAP | 24 | 71 | 99:1 | 85 |

EXAMPLE 4

Hydrogenation of Methyl 3-oxo-2-pentyl-1-cyclopentene-1-acetate

To a cooled solution of [Ru(COD)(COT)] (30.1 mg, 0.095 numole) in $CH_2Cl_2$ (5.0 ml) there was added dropwise, under stirring, a diethyl ether solution (54% weight) of $HBF_4$ (12.0 μl, 0.087 mml). (R)-(S)-JOSIPHOS (56.4 mg, 0.095 mmole) in $CH_2Cl_2$ (5.0 ml) was then added and the solution was allowed to stir for 6 h and then allowed to warm up to room temperature. Methyl 3-oxo-2-pentyl-1-cyclopentene-1-acetate was then added (catalyst relative to substrate:0.05%) in methyl tert-butyl ether (v/v=1:1) and the hydrogenation carried out under the usual conditions (90 bar). After 8.5 h there was obtained the desired product with a ratio cis/trans=99/1 and (+)-cis/(−)cis=88/12.

What is claimed is:

1. A ruthenium (II) catalyst comprising the reaction product of a ruthenium(II) complex, a chelating diphosphine, and an acid of formula H-Anion, wherein the Anion is a non-coordinating anion selected from the group consisting of $BF_4^-$, $B[3,5-(CF_3)_2C_6H_4]_4^-$, $PF_6^-$, $SbF_6^-$ and $AsF_6^-$;
the ruthenium complex and chelating diphosphine are present in equimolar amounts;
the acid is used in an amount of about 1 molar equivalent per mole of the ruthenium complex; and
the reaction occurs in the presence of hydrogen and under an oxygen-free atmosphere in a non-coordinating or weakly coordinating medium.

2. The catalyst according to claim 1, consisting essentially of the reaction product.

3. The catalyst according to claim 1, wherein the chelating diphosphline is a chiral diphosphine ligand.

4. The catalyst according to claim 3, wherein the ruthenium complex has the formula [(diene)Ru(allyl)$_2$] or [bis(pentadienyl)Ru].

5. The catalyst according to claim 3, wherein the ruthenium complex comprises [(COD)Ru(2-methylallyl)$_2$] or [Ru(COD)(COT)].

6. The catalyst according to claim 1, wherein the chelating diphosphine is selected from the group consisting of the chiral ligands known under the abbreviations of Me-DuPHOS, Et-DuPHOS, BINAP, TolBINAP, SKEWPHOS and JOSIPHOS.

7. The catalyst according to claim 6, wherein the chelating diphosphine ligand is selected from the group of chiral diphosplhines known under the abbreviations of Me-DuPHOS, SKEWPHOS and JOSIPHOS.

8. The catalyst according to claim 6, wherein the ligand is (R)-(S)-$CF_3$-JOSIPHOS.

9. The catalyst according to claim 7, wherein the ligand is (R,R)-(−)-Me-DuPHOS or (R)-(S)-JOSIPHOS.

10. The catalyst according to claim 1, wherein the non-coordinating anion is $BF_4^-$.

11. The catalyst according to claim 10, wherein the $BF_4^-$ is in the form of $HBF_4$.etherate.

12. The catalyst according to claim 1, wherein the weakly coordinating medium is a solvent selected from the group consisting of dichloromethane, dichloroethane, ethyl pivalate, methyl acetate, ethyl acetate, isopropyl acetate, acetone, 2-butanone, 3-pentanone, hexane, heptane, cyclohexane, cycloheptane, methyl tert-butyl ether, and mixtures thereof.

13. A process for preparing a ruthenium (II) catalyst which comprises reacting equimolar amounts of a ruthenium (II) complex and a chelating diphosphine with an acid of formula H-Anion, wherein Anion is at least one non-coordinating anion selected from the group consisting of $BF_4^-$, $B[3,5-(CF_3)_2C_6H_4]_4^-$, $PF_6^-$, $SbF_6^-$ and $AsF_6^-$, in the presence of hydrogen and under an oxygen-free atmosphere in a non coordinating or weakly coordinating medium, with the acid being used in an amount of about 1 molar equivalent per mole of the ruthenium complex.

14. The process of claim 13, wherein the chelating diphosphine comprises a chiral diphosphine ligand.

15. The process of claim 14, wherein the chelating diphosphine is selected from the group consisting of the chiral ligands known under the abbreviations of Me-DuPHOS, Et-DuPHOS, BINAP, TolBINAP, SKEWPHOS and JOSIPHOS.

16. The process of claim 13, wherein the ruthenium complex has the fomiula [(diene)Ru(allyl)$_2$] or [bis(pentadienyl)Ru].

17. The process of claim 13, wherein the ruthenium complex comprises [(COD)Ru(2-methylallyl)$_2$] or [Ru(COD)(COT)].

* * * * *